US008996318B2

(12) United States Patent
Beatty et al.

(10) Patent No.: US 8,996,318 B2
(45) Date of Patent: Mar. 31, 2015

(54) USING OLIGONUCLEOTIDE MICROARRAYS TO ANALYZE GENOMIC DIFFERENCES FOR THE PREDICTION OF HETEROSIS

(75) Inventors: Mary Beatty, Earlham, IA (US); James A. Janni, Johnston, IA (US); Jonathan E. Lightner, Des Moines, IA (US); J. Antoni Rafalski, Wilmington, DE (US)

(73) Assignees: Pioneer Hi-Bred International, Inc., Johnston, IA (US); E. I. du Pont de Nemours and Company, Wilmington, DE (US)

( * ) Notice: Subject to any disclaimer, the term of this patent is extended or adjusted under 35 U.S.C. 154(b) by 1166 days.

(21) Appl. No.: 12/344,887

(22) Filed: Dec. 29, 2008

(65) Prior Publication Data

US 2009/0170712 A1 Jul. 2, 2009

Related U.S. Application Data

(60) Provisional application No. 61/017,227, filed on Dec. 28, 2007.

(51) Int. Cl.
*G06F 19/18* (2011.01)
*C12Q 1/68* (2006.01)
*A01H 1/04* (2006.01)

(52) U.S. Cl.
CPC .................................. *C12Q 1/6809* (2013.01)
USPC ............................ 702/20; 435/6.11; 800/267

(58) Field of Classification Search
None
See application file for complete search history.

(56) References Cited

U.S. PATENT DOCUMENTS

| | | | | |
|---|---|---|---|---|
| 5,981,832 | A | 11/1999 | Johnson | |
| 6,455,758 | B1 | 9/2002 | Johnson | |
| 2007/0134678 | A1 | 6/2007 | Rees | |
| 2008/0083042 | A1* | 4/2008 | Butruille et al. | 800/267 |

FOREIGN PATENT DOCUMENTS

| | | | |
|---|---|---|---|
| WO | WO 00/42838 | | 7/2000 |
| WO | WO 01/07664 | A2 | 2/2001 |
| WO | WO 03/050748 | A2 | 6/2003 |
| WO | WO 2005/075668 | A1 | 8/2005 |
| WO | WO 2007/113532 | A2 | 11/2007 |

OTHER PUBLICATIONS

Springer et al. (Genome Research, vol. 17, p. 264-275, 2007).*

Flint-Garcia et al. (PLoS One 4(10):e7433. doi:10.1371/journal.pone.0007433).*

Korn et al. (Molecular plant, vol. 3, No. 1, p. 224-235, 2010).*

Belo et al. (Theor Appl Genet, vol. 120, p. 355-367, 2010).*

Aliferis et al. (AMIA 2002 Annual Symposium Proceedings, p. 7-11).*

Bilke, Sven et al., "Analysis of Comparative Genomic Hybridization Data on cDNA Microarrays" Microarray Data Analysis Methods and Applications, Mar. 2007, pp. 175-186, Humana@Humanapr.com.

Buffart, Tineke E., et al., "DNA Quality Assessment for Array CGH by Isothermal Whole Genome Amplification", Cellular Oncology, vol. 29, No. 4, 2007, pp. 351-359.

Fan, Ys et al., "Detection of Pathogenic Gene Copy Number Variations in Patients with Mental Retardation by Genomewide Oligonucleotide Array Comparative Genomic Hybridization", Hum. Mutat. Jul. 9, 2007, www.ncbi.nlm.nih.gov.

Gavora, J.S. et al., "Prediction of Heterosis from DNA Fingerprints in Chickens", Genetics Society of America, Oct. 1996, 144:777-784.

Jordan, D.R. et al., "Prediction of Hybrid Performance in Grain Sorghum Using RFLP Markers", Theor. Appl. Genet. (2003) 106:559-567.

Joshi, SP, et al., "Use of DNA Markers in Prediction of Hybrid Performance and Heterosis for a Three-Line Hybrid System in Rice". Biochem. Genet., Jun. 2001, 39(5-6):179-200. www.ncbi.nlm.nih.gov.

Li, Youjuan et al., "Analysis of Array CGH Data for Cancer Studies Using Fused Quantile Regression", Bioinformatics Advance Access published Jul. 20, 2007, pp. 1-8.

Paris, PL et al., "High Resolution Oligonucleotide CGH Using DNA from Archived Prostate Tissue", Prostate, Jul. 24, 2007, 67(13)1447-1455. www.ncbi.nlm.nih.gov.

Pinkel, Daniel et al., "Array Comparative Genomic Hybridization and Its Applications in Cancer", Nature Genetics Supplement, vol. 37, Jun. 2005, pp. S11-S17.

Schrag, Tobias A. et al., "Prediction of Single-Cross Hybrid Performance in Maize Using Haplotype Blocks Associated with QTL for Grain Yield", Theor. Appl. Genet. (2007), 114:1345-1355.

Shah, Sohrab P. et al., "Modeling Recurrent DNA Copy Number Alterations in Array CGH Data", Bioinformatics, vol. 23 ISMB/ECCB 2007, pp. i450-i458.

Uzarowska, Anna et al., "Comparative Expression Profiling in Meristems of Inbred-Hybrid Triplets of Maize Based on Morphological Investigations of Heterosis for Plant Height", Plant Mol. Biol. (2007) 63:21-34.

Vuylsteke, M. et al., "Chromosomal Regions Involved in Hybrid Performance and Heterosis: Their AFLP (R)-Based Identification and Practical Use in Prediction Models", Heredity, Sep. 2000, 85 Pt 3:208-18. XP-002522817.

Wikipedia, the free encyclopedia, "Comparative Genomic Hybridization", http://en.wikipedia.org/wiki/Comparative_genomic_hybridization, (4 pages), printed Jul. 31, 2007.

(Continued)

*Primary Examiner* — John S Brusca

(57) ABSTRACT

A novel method for prediction of the degree of heterotic phenotypes in plants is disclosed. Structural variation analyzes of the genome are used to predict the degree of a heterotic phenotype in plants. In some examples, copy number variation is used to predict the degree of heterotic phenotype. In some methods copy number variation is detected using competitive genomic hybridization arrays. Further, methods for optimizing the arrays are disclosed, together with kits for producing such arrays, as well as hybrid plants selected for development based on the predicted results.

3 Claims, 5 Drawing Sheets

(56) References Cited

OTHER PUBLICATIONS

Yao, Yingyin et al., "Identification of differentially Expressed Genes in Leaf and Root Between Wheat Hybrid and Its Parental Inbreds Using PCR-Based cDNA Subtraction", Plant Molecular Biology, (2005) 58:367-384.

Birchler, James A., et al., "In Search of the Molecular Basis of Heterosis", XP-002468493, The Plant Cell, vol. 15, 2236-2239, Oct. 2003.

Stuber, Charles W. et al., "Identification of Genetic Factors Contributing to Heterosis in a Hybrid From Two Elite Maize Inbred Lines Using Molecular Markers", Genetics 132:823-839 (Nov. 1992).

Xiong, L. Z. et al., "Relationships of differential gene expression in leaves with heterosis and heterozygosity in a rice diallel cross", Molecular Breeding 4:129-136, 1998.

International Search Report, Pioneer Hi-Bred International, PCT/US2008/088407, Apr. 21, 2009, 14 pages.

Eichler, Evan, Ph.D., et al., "Analysis of individual human geneomes has revealed an unexpected . . . "; Copy Number Variation and Human Disease, Nature Eduation 1(3), 2008.

Copy Number Variation, http://cn.wikepdia.org/w/index.php?oldid=459122817.

Vali, Ulo, et al., "Insertion-deletion plymorphisms (indels) as genetic markers in natural populations"; BMC Genetics 2008; 9:8.

Oxford Dictionary of Biology, Sixth Edition, excerpt pp. 179 and 339.

Schrider, Daniel R., et al., "Gene copy-number polymorphism in nature"; Proc. R. Soc. B.; doi 10.1098/rspb.2010.1180.

Microsatellite (genetics); http://cn.wikepdia.org/w/index.php?oldid=4555765331.

Carter, Nigel P., "As normal as can be?", Nature Genetics, vol. 36, No. 9, pp. 931-932, Sep. 2004.

Newman, Tera L., et al., "High-through put genotyping of intermediate-size structural variation"; HMG Advance Access published Feb. 23, 2006.

* cited by examiner

USING OLIGONUCLEOTIDE MICROARRAYS TO ANALYZE GENOMIC DIFFERENCES FOR THE PREDICTION OF HETEROSIS

CROSS REFERENCE TO RELATED APPLICATIONS

This application claims the benefit of U.S. Patent Application Ser. No. 61/017,227 filed Dec. 28, 2007, which is herein incorporated by reference in its entirety.

FIELD OF THE INVENTION

This invention relates to the field of plant molecular biology and plant breeding, particularly the prediction of the degree of heterotic phenotypes in plants.

BACKGROUND

Agricultural output has risen dramatically during the last half of the twentieth century. A large portion of this increase has been attributed to the development and use of hybrid seed varieties in core crops such as corn, sorghum, sunflower, alfalfa, canola and wheat. The success of hybrid seed varieties is due to a phenomenon called heterosis, where hybrid plants display a more desirable phenotype than either of the two inbred parental lines used to produce the hybrid plant. Heterosis has been observed in a number of plant traits including yield, plant height, biomass, resistance to disease and insects, tolerance to stress and others. These heterotic traits are polygenic in nature, resulting in their characteristic range of phenotypes, rather than traditional discrete Mendelian phenotypes. The polygenic nature of the traits results in complex patterns of inheritance such that the underlying components for the observed heterotic phenotypes is still a matter of debate in the plant science community.

Because of the economic value of heterosis, there have been several attempts to use molecular biology techniques to augment traditional hybrid plant breeding programs. The bulk of the efforts have focused on either mRNA (messenger RNA) or genomic DNA. The mRNA approach is extremely difficult as comparisons require tissue samples selected from the same portion of the plant, at the same developmental time, and in the same or highly similar environmental conditions. The process is further complicated as a researcher needs to determine which plant portion or developmental stage will yield the best results for predicting the degree of a particular heterotic phenotype of interest. As a result of these complications, mRNA-based predictions frequently have high levels of noise and have low accuracy in the prediction of the degree of a heterotic phenotype.

The use of genomic DNA to predict the degree of one or more heterotic phenotypes has been similarly disappointing. Initial efforts used subtractive hybridization or fluorescent in situ hybridization in order to identify copy number differences in inbred plant lines. These techniques do not produce easily quantifiable results and can only detect gross differences in copy numbers, such as a doubling or complete elimination. This is a significant problem in polyploid plants as chromosomal duplications and other evolutionary events have resulted in genes with multiple copies, some of which are pseudogenes, throughout the plant genome. These higher copy numbers greatly reduce the usefulness of the genomic DNA approaches as they are unable to accurately detect the addition or deletion of a single copy of a gene represented three or more times in the genome.

Another genomic approach has been the use of genetic markers to predict heterosis. In these techniques, RFLP markers as well as other traditional markers have been used. Researchers have attempted to use genetic markers to predict the degree of a heterotic phenotype with some success, so long as the potential parent plants belong to the same heterotic groups that were used in the initial crosses to generate the correlational data upon which the prediction is based. Once plants from other heterotic groups are used, the heterotic phenotype predictive ability of genetic markers greatly diminishes. The reason for the loss of predictive ability has been attributed to insufficient linkage of the markers to quantitative trait loci controlling the trait of interest, and a lack of gametic phase linkage disequilibrium between the marker and quantitative trait loci alleles. This diminished predictive ability severely limits the use of genetic markers in plant breeding programs.

Based on these efforts, the application of molecular biology techniques to the prediction of the degree of a heterotic phenotype has been problematic at best. Despite years of research, there has yet to be a satisfactory method developed.

Comparative Genome Hybridization (CGH) is a technique that has been employed to study chromosomal abnormalities in animal cells. A major area of CGH use has been in analyzing cancer mutations in an effort to better identify cancer cells in order to select more effective courses of therapy. CGH is particularly effective in animal cells as there are typically two copies of any given gene in the genome (one from each parent). Additionally, entire genomes for mammals are currently known. Researchers have been able to take advantage of the low duplication and genome sequence information to identify duplicated and deleted chromosomal regions. This information can then be used to identify the changes that have transformed normal cells into cancerous cells. However, the complete genome sequence of several major crops is not known at present. As a result, there has been little use of CGH in plants and doing so requires overcoming the numerous differences that arise when working with plant genomics.

SUMMARY

The present invention relates to the use of structural variation analyses of the genome, such as copy number variation analysis, detected for example by using comparative genomic hybridization, to predict the degree of a heterotic phenotype progeny in plants. In one aspect of the invention, groups of oligonucleotide probe molecules are contacted with plant genomic DNA and the resultant mixture of hybridized probes and genomic DNA is analyzed so as to determine probes that show differing hybridization levels between two different parents. The results are then used to predict the degree of a heterotic phenotype of progeny plants derived from the two parental lines. In another aspect of the invention, the predicted degree of a heterotic phenotype is used in the development of hybrid plants. In yet another aspect of the invention, a subset of oligonucleotide probe molecules that are good predictors of the degree of a heterotic phenotype are selected from a larger population of oligonucleotide probe molecules and the selected subset is then used in future assays to predict the degree of a heterotic phenotype. Another aspect of the invention is a kit comprising the selected oligonucleotide probe molecule subset that can be used for the prediction of the degree of a heterotic phenotype in plant lines. Other features will be discussed in greater detail in the description below.

DETAILED DESCRIPTION

Figure 1:
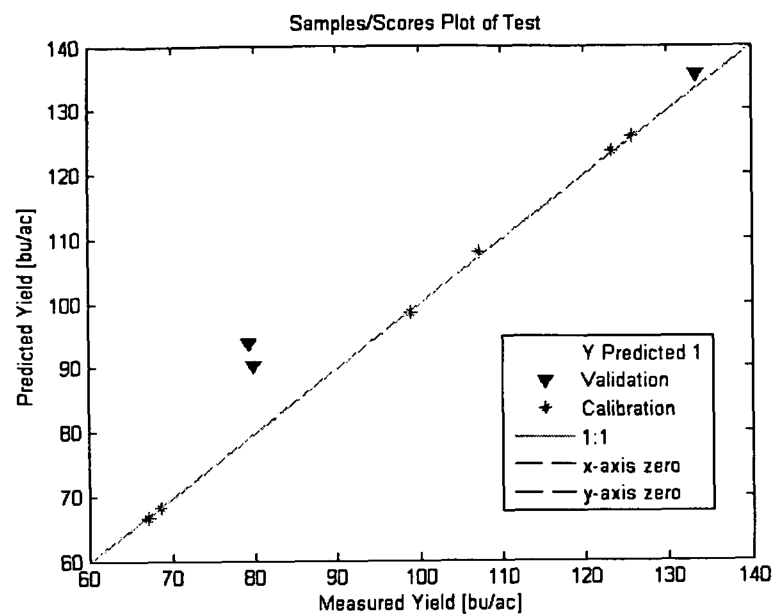
FIG. 1 shows yield predictions based on a PLS regression model built using the intensity ratios selected from the genetic algorithm and three latent variables. This PLS regression model was used to predict yield for three additional inbreds: PHBE2, PHHB4 and PHB37, hybridized on two 44,000 oligonucleotide probe arrays.

The following terms will be used frequently in the description that follows. The following definitions are provided to facilitate understanding of the disclosure.

"Coding regions" means the regions of an organism's genome that code for proteins or RNA molecules, wherein the coding regions and/or the RNA may include introns, exons, regulatory sequences, and 5' and 3' untranslated regions.

"Copy number variation" (CNV) is a segment of DNA for which copy-number differences have been found by comparison of two or more genomes, or comparison to a reference sequence. The term CNV encompasses other terminology to describe variants including large-scale copy number variants (LCV), copy number polymorphisms (CNP) and intermediate-sized variants (ISV).

"F1 hybrid plant variety" means the first filial generation resulting from crossing two distinct parental lines.

"Heterosis-related phenotype" means an observable trait in a plant where the phenotype exhibited in hybrid plants is more desirable when compared to the corresponding phenotype exhibited in homozygous parent plants.

"Hybridization intensity" means a measure of the quantity of genomic DNA hybridized to an oligonucleotide probe molecule based on a quantifiable marker linked to the prepared genomic DNA. The quantity of prepared DNA binding to the oligonucleotide probe molecule reflects the sequence similarity between the genomic DNA and the oligonucleotide probe molecule as well as the copy number of the region of the genomic DNA bound to the oligonucleotide probe molecule.

"Hybridization pattern" means a collection of the hybridization intensities for each unique oligonucleotide probe molecule in a plurality of oligonucleotide probe molecules after the probe molecules have been placed in contact with a sample of DNA or RNA.

"Oligonucleotide array" means a plurality of oligonucleotide probe molecules stably associated with a solid support.

"Oligonucleotide probe molecules" means short sequences of DNA and/or RNA that will selectively hybridize with a prepared sample containing DNA and/or RNA.

"p-value" means a measure of probability that an observed difference between hybridization intensities happened by chance. For example, a p-value of 0.01 (p=0.01) means there is a 1 in 100 chance the result occurred by chance. The lower the p-value, the more likely it is that the difference observed between hybridization intensities was caused by actual differences between the two samples.

"Prepared genomic DNA" means DNA from an organism that has been digested and/or sheared and labeled with a detectable marker. Further manipulation of the DNA may be made, including PCR amplification of the DNA before the DNA is digested and/or sheared, between the digesting/shearing step and the labeling step, or after the labeling step. Techniques may also be applied to select for a subset of genomic DNA, such as, for example, methyl sensitive restriction enzyme screening, use of melting curves and selection based on speed of refolding, use of Cot DNA, and the like. Such subsets of genomic DNA are included within this definition.

"Structural variation" refers to the changes in genetic structure that occur in the genome. A wide range of structural variation can occur in the genome including deletions, insertions, duplications, and inversions. These variations range in size, and are typically grouped 1-500 bp, (fine-scale), 500 bp-100 kb (intermediate-scale), and >100 kb (large-scale) in size. As used herein, structural variation does not include RFLPs.

Any method can be used to detect, quantify, and/or analyze copy number variation between two or more genomes. For example copy number variation can be discovered by cytogenetic techniques such as fluorescent in situ hybridization, comparative genomic hybridization, array comparative genomic hybridization, large-scale SNP genotyping, whole genome sequencing, paired-end mapping, clone-end resequencing, in silico analyses, or combinations thereof. Optionally, computer or statistical analyses and/or modeling may be used in conjunction with any CNV methods.

Copy number variation detection is distinct from typical single nucleotide polymorphism detection. Hybridization with short olugonucleotides on solid surfaces may be used to detect single nucleotide polymorphisms (SNP) (Chee, et al., (1996) *Science* 274:610-614). In this SNP detection application, 20-22 mer oligonucleotides are usually used to maximize the ability to detect single mismatches between the probe and target (Lipshutz, et al., (1995) *Biotechniques* 19:442-447). Longer oligonucleotides, such as the 60-mers used in Example 1 for CGH hybridize with very similar affinity to perfectly matched targets and to targets with one or even two mismatches. Therefore such oligonucleotide probes are not suitable for SNP detection. These longer probes are typically very sensitive to the presence or absence of the target sequence, or to the large changes in the quantity of the target sequence, and are therefore useful for detecting copy number variation. In maize, SNP polymorphisms occur in coding regions with an overall frequency of less than 1 SNP/100 bp (Ching, et al., (2002) *BMC Genet* 3:19). Most of the probes used in Examples 1-2 contain 0-1 mismatch as compared to the genomic DNA, and hybridize well to the target. In the rare occasions of deletion or multiplication of the target in the genome, such probes will be expected to show numerically large ratios of hybridization signal between different inbreds, and to deviate from the expected 1:1 ratios expected for targets that are identical or contain 1 mismatch. In Examples 1-2 probes with large observed hybridization ratio between different maize inbreds were selected, although no specific representation is made as to molecular differences underlying such hybridization ratios except that they are unlikely to be due to the presence of 1-2 bp differences between probe and target.

In one example the method described herein utilizes CGH to predict the degree of one or more heterotic phenotypes in hybrid plant varieties. The disclosed method allows for selection of inbred parental lines, while avoiding the need to perform resource-consuming test crosses across a large number of potential parental lines. This method may be used with a number of oligonucleotide probe molecules ranging from a large to an unexpectedly low number of oligonucleotide probe molecules for prediction of the degree of heterotic phenotypes. The selection of oligonucleotide probe molecules can be facilitated by the use of an optimization procedure, an example of which is described herein. Additionally, the disclosed CGH method provides an unexpectedly significant increase in predictive ability over techniques currently used in plant breeding. The use of CGH also eliminates many of the difficulties experienced in the use of mRNA for the prediction of the degree of one or more heterotic phenotypes in plants, as the genomic DNA is the same in every somatic cell in the plant (apart from gametophytes) regardless of the developmental stage, environmental conditions, or the tissue sampled. These results indicate that CGH is a reliable assay for the prediction of the degree of one or more heterotic phenotypes in plants.

A review of CGH, including the general considerations and a description of the technology, may be found in Pinkel and Albertson, (2005) *Nature Genetics* 37:S11-S17, and is incorporated by reference herein in its entirety. The familiarity with CGH technology of those of ordinary skill in the art is therefore assumed in the foregoing description. Using the method claimed to predict the degree of one or more heterotic phenotypes includes the selection of a plurality of oligonucleotide probe molecules, obtaining sample genomic DNA, preparing the genomic DNA, hybridization of the sample DNA with the oligonucleotide probe molecules, detection of the resultant hybridization intensities, comparison of the intensities detected with results from one or more other samples with known heterotic phenotypes and predicting the heterotic phenotype of progeny plants derived from the plants that provided the genomic DNA.

One way to improve the disclosed methods is the selection of the plurality of oligonucleotide probe molecules. In one example the plurality of oligonucleotide probe molecules comprises an oligonucleotide array. In some examples, an oligonucleotide array designed for mRNA analysis can be used as the plurality of oligonucleotide probe molecules. Optionally, the oligonucleotide array comprises oligonucleotide probe molecules covering the entire plant genome, with redundant sampling of each region of the genome as well as positive and negative controls. In some examples, the oligonucleotide array comprises oligonucleotide probe molecules that are known to be predictive of the degree of a heterotic phenotype in the target plant.

When selecting oligonucleotide probe molecules for use, factors such as molecule size, molecule composition, and the genomic location of the molecules selected may be considered. Regarding molecule size, smaller molecules are less able to hybridize with sequences that contain mismatches, including insertions, deletions, or substitutions, but are less susceptible to the formation of secondary structures. Longer oligonucleotide probe molecules are more able to hybridize to DNA containing mismatches, but are more susceptible to the formation of secondary structures.

Oligonucleotide probe molecules that form secondary structures are less able to hybridize with the prepared sample genomic DNA. The prediction of secondary structures in oligonucleotide sequences is well known and there are several software packages that are able to predict secondary structure formations and thermodynamic properties such as mFOLD (Zuker, et al. (1999) *Algorithms and Thermodynamics for RNA Secondary Structure Prediction: A Practical Guide in RNA Biochemistry and Biotechnology*, Barciszewski and Clark, eds., NATO ASI Series, Kluwer Academic Publishers) and RNAfold (Vienna RNA Package; Hofacker, et al., (1994) *Monatshefte f. Chemie* 125:167-188; Zuker and Stiegler, (1981) *Nucl Acids Res* 9:133-148). Using these tools, it is possible to balance the coverage of genomic locations with the likelihood of secondary structure formation. When using a comprehensive oligonucleotide probe molecule set, the oligonucleotide probe molecules may be selected such that the entire plant genome is covered multiple times with probes that are not likely to form secondary structures. When using a smaller oligonucleotide probe molecule set, the probes may be selected to cover the genomic regions of interest with redundant coverage while still maintaining a low likelihood of forming secondary structures.

The oligonucleotide probe molecules used in the methods are generally between 20 and 100 nucleotides in length. In some examples, the oligonucleotide probe molecules are 60 nucleotides in length. Of course, the oligonucleotide probe molecules in a given plurality need not all be of uniform length, and in some examples having oligonucleotide probe molecules of differing lengths may utilize or compensate for the varying characteristics of oligonucleotide probe molecules of various lengths described above.

The quality of data produced by the method can be increased by incorporating more than one oligonucleotide probe molecule per gene or genomic region of interest. The inclusion of these redundant oligonucleotide probe molecules provides internal checks to determine if the differing hybridization intensities are the result of a difference in copy number of a gene or chromosomal region or random noise. In some examples, more than one oligonucleotide probe molecule per gene or DNA region of interest is included in the plurality of oligonucleotide probe molecules. In some examples three oligonucleotide probe molecules are used for each gene or region of interest.

The process of creating oligonucleotide arrays is well known and a number of commercial machines are available for creating oligonucleotide arrays, such as the BioOdyssey Calligrapher MiniArrayer by BioRad. Additionally, there are a number of commercial services that will create oligonucleotide arrays from a list of oligonucleotide probe molecule sequences, such as the SurePrint microarray printing service by Agilent. The plurality of oligonucleotide probe molecules typically includes at least about one hundred oligonucleotide probe molecules but can include any number of oligonucleotide probe molecules between about 100 to about 80,000 oligonucleotide probe molecules, or more if greater testing ranges are desired. Additionally, the plurality of oligonucleotide probe molecules can be designed to include any number of positive or negative controls to ensure validity of the data acquired by use of the plurality of oligonucleotide probe molecules.

Another aspect of the claimed method is the preparation of genomic DNA prior to contact with the plurality of oligonucleotide probe molecules. Preparation and labeling of genomic DNA is well known, and kits for the preparation of genomic DNA for CGH are available, such as the "Genomic DNA Labeling Kit PLUS" (Agilent). Genomic DNA is isolated from each parent line and individually labeled. Typically, approximately equal quantities of DNA from each parent are used, otherwise the accuracy of the results regarding differences in copy number may suffer, and thus be potentially less effective as predicting the degree of a heterosis-related phenotype of interest. The amount of isolated genomic DNA required depends on a number of factors, including the size of the oligonucleotide array and the protocols used. When a medium-sized oligonucleotide array (between about 40,000 and 100,000 oligonucleotide probe molecules) is used following standard protocols, the amount of genomic DNA used is typically between 0.2 and 3.0 μg. When the sample does not contain sufficient genomic DNA for direct hybridization, any well known amplification technique (e.g., PCR amplification) can be used to increase the quantity of prepared genomic DNA.

Typically, once a sufficient quantity of genomic DNA is available, the genomic DNA is fragmented using standard techniques such as digestion with at least one restriction endonuclease, mechanical shearing, or a combination thereof, to provide genomic DNA fragments of relatively uniform length. The fragmented, genomic DNA sample may then be purified, quantified, and concentrated using standard techniques. The resultant concentrated genomic DNA fragments may be labeled in a PCR reaction using random primers and labeled dUTP molecules with each parent having a unique fluorescent label. If using different oligonucleotide arrays for each parent, it is then possible to use the same label with both parents, although typically both samples are analyzed on a single array. Optionally, it is also possible to use more than two labels for additional potential parents.

Generally genomic DNA is extracted from tissue samples that are either fresh or frozen. Any tissue storage method can be used, the goal being to reduce the degradation of the genomic DNA. Additionally, signal strength can be improved by the elimination of low-complexity DNA using standard techniques such as methyl sensitive restriction enzyme screens of the genome, the use of melting curves with selection based on the speed of refolding, and the use of Cot DNA to precipitate low complexity sequences.

After DNA preparation, the prepared DNA is contacted with the plurality of oligonucleotide probe molecules. The prepared and labeled genomic DNA is typically contacted with an oligonucleotide array under strict hybridization conditions. Techniques and conditions required for hybridization of sample DNA to oligonucleotide arrays are known, and kits containing the requisite solutions and buffers are commercially available, such as the Oligo aCGH/ChIP-on-chip Hybridization Kit (Agilent, Santa Clara, Calif., USA). Prepared genomic DNA from the parents is typically hybridized to the same oligonucleotide array. Alternatively, the prepared and labeled genomic DNA of each parent may be hybridized to different arrays at different times so long as the different arrays contain at least some subset of common oligonucleotide probe molecules. In some examples the DNA from each parent is hybridized to two separate but identical array of oligonucleotide probe molecules under the same hybridization conditions.

After contacting the prepared DNA with the plurality of oligonucleotide probe molecules, the hybridization intensities generated by the hybridization of the genomic DNA with the oligonucleotide probe molecules are detected. Optionally, a commercial microarray scanner (such as an Agilent DNA Microarray Scanner) is used to detect the hybridization intensities. The detected hybridization intensities are typically displayed on software associated with the scanner and can be optionally exported into any number of file formats for advanced processing. The data analysis software can generate statistics based on the detected hybridization intensities. This enables a researcher to determine the number of probes displaying differing hybridization intensities and the degree of the intensity differences. In some examples, the software is used to determine the number of differences, the fold difference, or both, of oligonucleotide probe molecules displaying a greater than 1.5-fold difference in hybridization intensity. Optionally, the software can be used to determine the number of oligonucleotide probe molecules displaying at least a 2 fold difference in hybridization intensity. In some examples, the software can be used to determine the number of oligonucleotide probe molecules displaying a greater than three-fold, but less than ten-fold difference in hybridization intensity. Of course, other values can be used for either the minimum fold difference and/or the maximum fold difference, if one wanted to either narrow or broaden the group of relevant hybridization intensities. For example, minimum fold differences may include any value between a 1.5 fold difference and a 10 fold difference, and the maximum fold difference may include any value between 1.5 fold difference and a 50 fold difference. These minimum and maximum cutoffs can either be used independently (e.g., all oligonucleotide probe molecules displaying a difference in hybridization intensity greater than 1.7) or together (e.g., all oligonucleotide probe molecules displaying a greater than 2.1 but less than 11.4 fold difference) to provide data sets for further processing.

In another example, whole genome sequencing methods can be used to detect copy number variation. Whole genome shotgun sequencing of small (4000 to 7000 bp) genomes was in use in 1979 (Staden, (1979) *Nucl Acids Res* 6:2601-2610). The methodology has evolved to enable sequencing of larger more complicated genomes, including the fruit fly genome and the human genome. In general, high molecular weight DNA is sheared into random fragments, size-selected (usually 2, 10, 50 and 150 kb), and cloned into an appropriate vector. The clones are sequenced from both ends, typically using a chain termination method to yield two short sequences. Each sequence is called an end-read or read and two reads from the same clone are referred to as mate pairs. The chain termination method typically produces reads of about 500-1000 bases, therefore mate pairs rarely overlap. The original sequence is reconstructed from all of the reads using sequence assembly software. Overlapping reads are collected into longer composite sequences known as contigs. Contigs can be linked together into scaffolds by following connections between mate pairs. The distance between contigs can be inferred from the mate pair positions if the average fragment length of the library is known and has a narrow window of deviation. Many sequencing technologies are available using gel methods, capillary methods, bead methods, or array methods. Rapidly advancing sequencing technologies include sequencing by synthesis, parallel bead arrays, electronic microchips, biochips, parallel microchips, sequencing by ligation, single DNA molecule sequencing, and nanopore-sequencing. In this example, deletions/insertions would be detected by aligning the sequences to a reference genome. CNVs would be detected by counting the number of times a tag/sequence was observed and then comparing the counts to another sample or reference genome.

An in silico strategy was used to compare two human genomes at the DNA sequence level (Tuzun, et al., (2005) *Nat Genet* 37:727-732). The human genome sequence in NCBI was the reference genome. Approximately 67% of this reference sequence was from a single DNA library (the RPCI-11 BAC library) from a single individual. The second genome comprised pairs of end-sequence reads from >500,000 fosmid clones of the G248 DNA library. This DNA library was derived from an anonymous North American female of European ancestry. Since the sizes of fosmid clones are tightly regulated at about 40 kb, it was expected that pairs of end sequences for any given fosmid clone would align to the reference sequence with about a 40-kb spacing. Significant deviation of the alignment spacing (i.e., <32 kb or >48 kb) suggested the presence of a CNV at that locus. Using this criterion 241 CNVs were identified, with most in the size range of 8 kb to 40 kb, and 80% of these were not previously identified. Also, most of these CNVs were below the expected resolution of the array platforms used in earlier CNV studies. One advantage over array-based methods is that the in silico approach also detects other structural genomic variants, for example inversions. These structural variants can be detected by consistent discrepancies in the aligned orientation of multiple paired end sequences.

Chemometrics is the application of mathematical or statistical methods for experimental design and/or the analysis of data. Chemometrics can be used to identify further information from these data using various methods including statistics, pattern recognition, modeling, structure-property-relationship estimations, or combinations thereof. For example, the data can be hybridization data, hybridization intensity, p-values for intensity measures, hybridization intensity ratios, normalized data, sequencing data, sequence analysis output such as contigs, alignments, similarity scores, expected value scores, p-values, indels, or other data generated by a method to detect genomic structural variations.

In some examples, data analysis software is used to calculate p-values based on the measured differences in hybridization intensity. These values may be used as substitutes for or in addition to the fold differences in the intensity between oligonucleotide probe molecules. When using the p-value in lieu of fold difference one can increase the stringency by decreasing the maximum p-value considered. For example, a researcher may wish to apply a low stringency cut-off by selecting all oligonucleotide probe molecules where the difference in hybridization intensity yielded a p-value less than 0.1. The stringency can be increased by lowering the maximum p-value to 0.05, 0.01, 0.001 or any value within the range of 0.01 to 0.001.

Once the data is collected, the degree of a heterotic phenotype can be predicted based on the results obtained. This prediction is accomplished by comparing the number of probes meeting the user defined threshold during analysis to the number of probes displaying meeting the same criteria in other hybridizations involving parents where the heterotic phenotype in resultant F1 hybrid progeny is known. Additionally, common statistical techniques, such as linear regression, may be used to perform the prediction.

Optionally, the predicted degree of one or more heterotic phenotypes can be used to select parental lines for development of F1 hybrid plant lines as part of a plant breeding program. Modern plant breeding programs take a wide variety of factors into account when selecting plants for breeding. In another example, the predicted degree of a heterotic phenotype is included among the factors and forms at least part of the rationale for selecting two parental lines for breeding in a commercial or other plant breeding program.

The methods can be used to develop a plurality of oligonucleotide probe molecules specialized for the prediction of the degree of one or more heterotic phenotypes. The identification of oligonucleotide probe molecules that are predictive of heterotic phenotypes in a target plant can be accomplished through the use of an empirical approach. In one example a number of F1 hybrid plant lines are created and grown under controlled conditions and the heterotic phenotype of interest is measured. Using an oligonucleotide array, typically one that covers a greater amount of the plant genome, CGH is performed for the parental lines. The resultant hybridization intensities are analyzed to determine the oligonucleotide probe molecules that demonstrate better ability to predict the degree of heterotic phenotype in the measured F1 hybrid plant lines. The oligonucleotide probe molecules that are better predictors are then used in an improved oligonucleotide array to predict the degree of a heterotic phenotype, either in lieu of or in addition to a comprehensive oligonucleotide array as described above.

In some examples, the analysis of the hybridization intensities is performed using an iterated evolutionary computational approach. In this approach, the software forms arbitrary sub-groupings of the oligonucleotide probe molecules and uses regression analysis to determine the predictive ability of the probe subsets. The regression may be coupled with a machine learning method and used to select the sub-groupings of oligonucleotide probe molecules that demonstrate a better performance in predicting heterotic phenotypes. Types of regression analyses that may be used include, for example, principal component regression, classic least squares, inverse least squares, and partial least squares. Machine learning methods that may be used include, for example, support vector machines and neural networks. Regression and machine learning may be used individually or in combination to perform the analysis. Hybridization intensity predictor selection in the regression analysis alone can be done as shown in some examples using variable of importance projection within the PLS representation space. The process of forming subgroups and selecting better predictors through the use of regression and machine learning may also be repeated until a user-defined point. In some examples, the process is iterated until there are only slight increases in the predictive ability of the subsets. In other examples, the process is iterated until there is no increase in the predictive ability of the subsets.

Optionally, an oligonucleotide array comprising the identified oligonucleotide probe molecules is created. In some examples the created oligonucleotide array is part of a kit for the prediction of the degree of one or more heterotic phenotypes in a plant that is available for commercial sale or internal use.

The following examples further illustrate the current invention and are not intended to limit the claims in any way. The present invention can be practiced using many different variations and has been shown by means of illustrative examples. The invention is not limited to the embodiments disclosed but also includes all modifications, equivalents, and alternatives falling within the spirit and scope of the invention as set forth in the claims.

EXAMPLE 1

Comparative Genome Hybridization (CGH) in Maize

Genomic DNA:

Genomic DNA was obtained from the following maize inbreds: PHP38, PHK29, PHW61, PHR03, PHW52, PHN46, PHHB4, PHBE2, PHB37, PH1FA, PHT11 and PHB47. Total cellular DNA was isolated from fresh-frozen leaf samples by using DNEASY Plant Mini Kits (Qiagen) cellular DNA extraction kits including an incubation with RNAseA following the instructions of the manufacturer. Samples were quantitated with a spectrophotometer and ran on an agarose gel to check for integrity.

aCGH:

For each CGH hybridization, 2 μg of genomic DNA was digested with AluI and RsaI restriction enzymes (Promega). After a two-hour incubation, the samples were heated to 65° C. for 20 minutes to inactivate the enzymes. The fragmented DNA was labeled via a random primed labeling reaction (Agilent Oligonucleotide Array-Based CGH for Genomic DNA Analysis, v4.0) that incorporated Cy3-UTP into the product. The labeled DNA was filtered with a MICROCON YM-30 column (Millipore) centrifugal filter device to remove unincorporated nucleotides. Samples were quantitated with a Hitachi spectrophotometer to measure yield and dye incorporation rates. Hybridization and blocking buffers (Agilent Technologies) were added to the samples prior to being denatured at 95° C. for 3 minutes and incubated at 37° C. for 30 minutes. Each sample was hybridized to an array for 40 hours at 65° C. while rotating at 10 rpm. The arrays were disassembled and washed in Oligo aCGH Wash Buffer 1 (Agilent Technologies) at room temperature for 5 minutes. A second wash was performed in Oligo aCGH Wash Buffer 2 (Agilent Technologies) for 1 minute at 37° C. Slides were then dipped in Acetonitrile and air dried. An Agilent G2505B DNA microarray scanner was utilized to capture the TIF images.

Oligonucleotide Microarrays:

Custom 44K microarrays (Agilent Technologies) containing 82,272 unique 60 mer oligos spanning two microarrays targeting expressed sequences of the maize genome were utilized for the hybridization of the following inbreds: PHP38, PHK29, PHW61, PHR03, PHW52, PHN46, PHHB4, PHBE2 and PHB37. Additionally, a custom 2×105K microarray (Agilent Technologies) containing 102,349 unique 60 mer oligos, of which 82,272 oligos were represented on the previous 44K arrays, was utilized for hybridization of the following inbreds: PHP38, PHK29, PHW61, PHR03, PHW52, PHN46, PHHB4, PHBE2, PHB37, PH1FA, PHT11 and PHB47.

Image and Data Analysis:

The microarray images were visually inspected for image artifacts. Feature intensities were extracted, filtered, and normalized with Agilent's Feature Extraction Software (version 9.5.1). Further quality control was performed utilizing data analysis tools in the ROSETTA RESOLVER (Rosetta Biosoftware) suite of bioinformatics tools.

Nebulization vs RE Digestion

Samples were randomly sheared via nebulization. 4 to 6 μg of purified DNA samples, in a final volume of 50 μl, were mixed in the nebulizer with 700 μl of nebulization buffer (25% glycerol, 50 mM Tris-HCl, 15 mM $MgCl_2$). The nebulizer was chilled on ice, and connected to a compressed air source. Air was delivered at a pressure of 32 psi for 6 min. The nebulizer was spun down and the DNA solution recovered. DNA was purified on one QIAQUICK® (Qiagen) PCR purification column and eluted in 30 μl of 10 mM Tris-HC1 pH 8.5. 0.5 μg of randomly sheared DNA was used for the labeling and hybridization steps previously described.

After hybridization, the data from the restriction enzyme (RE) digest and randomly sheared samples were compared to determine if there is any difference with sample prep methodology. The comparison of nebulized samples vs. RE digested samples showed a high correlation of fold changes (R squared=0.89). Therefore, there are no major differences with the data when either sample prep method is utilized.

EXAMPLE 2

Regression Analyses

The CGH array intensity ratios, values, accession numbers and oligonucleotide probe sequences were exported in ASCII text format using ROSETTA RESOLVER 6.0 (Rosetta Biosoftware, Seattle, Wash.) bioinformatic software. The CGH intensities were imported and aligned for each inbred and array in the Matlab (ver. 7.4.0, Mathworks, Natick, Mass.) technical computing environment using both the accession numbers and oligonucleotide sequences. The genetic algorithm intensity ratio selection using partial least squares regression analysis was performed using the PLSToolbox 4.0 (Eigenvector Research, Wenatchee, Wash.) in the Matlab workspace. All calculations were run on a Dell Latitude D620 with 1.8 GHz Intel duo core processor using multi-threaded mode.

Intensity ratio values from the two 44,000 oligonucleotide probe arrays described above were assembled for the inbreds PHB73, PHW61, PHR03, PHK29, PHW52 and PHN46. For the exemplary method described here, p-values less than 0.01 were used to reduce the number of genetic algorithm predictive candidate intensity ratios from 82435 to 2786. All intensities and intensities selected by fold change criteria have also been used for inputs for the genetic algorithm.

The genetic algorithm applied to predictive intensity ratio selection was the gaselctr.m function from the PLSToolbox. The algorithm was applied to an initial population size of 256 unique intensity ratio sets with 10% of the 2786 ratios selected in each individual. Partial least squares regression (PLS) of the yield to the selected intensity ratios was performed for yield prediction. Intensity ratio sets were ranked by their PLS yield prediction error. One hundred generations of double crossover combining using the 128 best ranking individual intensity ratio sets were performed ten times. The number of latent variables in the PLS regression was set to a maximum of three. The 201 intensity ratios selected from this genetic algorithm variable selection method predicted yield with the least root mean square error in leave one out cross validation among the 100,000's of intensity ratio sets tested by the genetic algorithm and a regression model built with all of intensity ratios.

A PLS regression model was built using the intensity ratios selected from the genetic algorithm and three latent variables. This PLS regression model was used to predict yield for three additional inbreds, PHBE2, PHHB4 and PHB37, hybridized on two 44,000 oligonucleotide probe arrays. These yield predictions were a validation of the model and intensity ratio selection method. The predictions are shown in FIG. 1. The prediction comparisons indicated with a triangle are for the inbreds that are not a part of the regression model. The asterisks indicate the prediction of the calibration samples.

Figure 2:
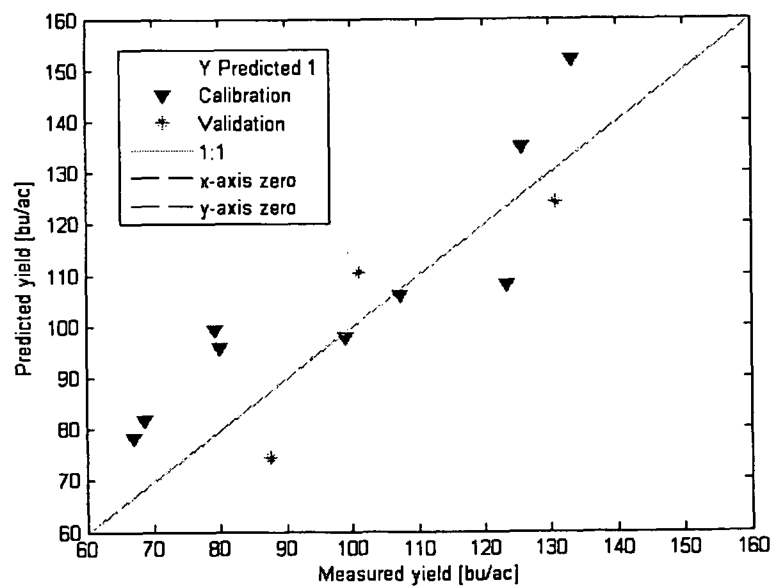
FIG. 2 shows yield predictions based on a PLS regression model built using the genetic algorithm selected intensity ratios for all nine of the inbreds: PHN46, PHR03, PHB73, PHW52, PHK29, PHW61, PHBE2, PHHB4 and PHB37, and ratios of six of the inbred compared to a replicate measure of PHP38, PHN46, PHR03, PHB73, PHW52, PHK29 and PHW61. The number of latent variables was increased to five and autoscaling was performed to account for this noise. Mean centering was performed on the yield data.

A PLS regression model was then built using the genetic algorithm selected intensity ratios for all nine of the inbreds, PHN46, PHR03, PHB73, PHW52, PHK29, PHW61, PHBE2, PHHB4 and PHB37, and ratios of six of the inbred compared to a replicate measure of PHP38, PHN46, PHR03, PHB73, PHW52, PHK29 and PHW61. The replicates contributed intensity ratio noise to the model building. The number of latent variables was increase to five and autoscaling was performed to the intensity ratio to account for this noise. Mean centering was performed on the yield data. The predictions are shown in the FIG. 2 below for the intensity ratios derived from the arrays with 20,000 additional oligonucleotides from coding regions of the genome. The new arrays were hybridized for the nine inbreds already mentioned and three new inbreds PH1FA, PHT11 and PHB47. The comparisons of predicted yield and measured yield for the new inbreds are indicated by the asterisks. The PLS regression model calibration samples are indicated by the triangles. The root mean square error of prediction for the new inbred was 9 bu/ac.

The predicted heterosis values will be an approximation of change in yield (bu/ac). This method can be used as a preliminary screening of germplasm, particularly new germplasm, and may be used to select a smaller set for experimental measurement of heterosis. In this application, the method provides a reduction of the number of lines to be evaluated in the field.

This method was validated using a larger set of samples, and with more diverse genotypes. CGH data was generated essentially as described in Example 1, by hybridization against maize CGH arrays in 2×105K format. Samples were for CGH were taken from 14 R2 experiments containing plants from 3 relative maturity groups, representing 181 genotypes (91 stiff stalk, 90 non-stiff stalk inbreds) which produced 914 hybrids. The data was analyzed to identify oligonucleotides associated with heterosis using phenotypic data including yield, ear height, moisture, test weight, stay green, plant height, stock lodging and root lodging. Data from this analysis was cross-validated with mapping data when available. For stiff-stalk inbred A vs. 36 non-stiff stalk inbreds, putative predictive oligo sets for yield, ear height, moisture and plant height were identified using the variable importance projection method described in Example 5, and shown in FIGS. 6-9).

EXAMPLE 3

Comparison of Genomic DNA Preparation Methods

Genomic DNA:

Genomic DNA was obtained from the following maize inbreds: PHP38, PHK29, PHW61, PHR03, PHW52, PHN46, PHHB4, PHBE2, PHB37, PH1FA, PHT11 and PHB47. Total cellular DNA was isolated from fresh-frozen leaf samples by using DNEASY Plant Mini Kits (Qiagen) cellular DNA extraction kits, including an incubation with RNAseA following the instructions of the manufacturer. Samples were quantitated with a spectrophotometer and ran on an agarose gel to check for integrity.

aCGH:

For each CGH hybridization, 2 μg of genomic DNA was digested with AluI and RsaI restriction enzymes (Promega). After a two-hour incubation, the samples were heated to 65° C. for 20 minutes to inactivate the enzymes. The fragmented DNA was labeled via a random primed labeling reaction (Agilent Oligonucleotide Array-Based CGH for Genomic DNA Analysis, v4.0) that incorporated Cy3-UTP into the product. The labeled DNA was filtered with a MICROCON YM-30 column (Millipore) centrifugal filter device to remove unincorporated nucleotides. Samples were quantitated with a Hitachi spectrophotometer to measure yield and dye incorporation rates. Hybridization and blocking buffers (Agilent Technologies) were added to the samples prior to being denatured at 95° C. for 3 minutes and incubated at 37° C. for 30 minutes. Each sample was hybridized to an array for 40 hours at 65° C. while rotating at 10 rpm. The arrays were disassembled and washed in Oligo aCGH Wash Buffer 1 (Agilent Technologies) at room temperature for 5 minutes. A second wash was performed in Oligo aCGH Wash Buffer 2 (Agilent Technologies) for 1 minute at 37° C. Slides were then dipped in Acetonitrile and air dried. An Agilent G2505B DNA microarray scanner was utilized to capture the TIF images.

Oligonucleotide Microarrays:

Custom 44K microarrays (Agilent Technologies) containing 82,272 unique 60 mer oligos spanning two microarrays targeting expressed sequences of the maize genome were utilized for the hybridization of the following inbreds: PHP38, PHK29, PHW61, PHR03, PHW52, PHN46, PHHB4, PHBE2 and PHB37. Additionally, a custom 2×105K microarray (Agilent Technologies) containing 102,349 unique 60 mer oligos, of which 82,272 oligos were represented on the previous 44K arrays, was utilized for hybridization of the following inbreds: PHP38, PHK29, PHW61, PHR03, PHW52, PHN46, PHHB4, PHBE2, PHB37, PH1FA, PHT11 and PHB47.

Image and Data Analysis:

The microarray images were visually inspected for image artifacts. Feature intensities were extracted, filtered, and normalized with Agilent's Feature Extraction Software (version 9.5.1). Further quality control was performed utilizing data analysis tools in the ROSETTA RESOLVER (Rosetta Biosoftware) suite of bioinformatics tools.

Nebulization vs RE Digestion

Samples were randomly sheared via nebulization. 4 to 6 μg of purified DNA samples, in a final volume of 50 μl, were mixed in the nebulizer with 700 μl of nebulization buffer (25% glycerol, 50 mM Tris-HCl, 15 mM $MgCl_2$). The nebulizer was chilled on ice, and connected to a compressed air source. Air was delivered at a pressure of 32 psi for 6 min. The nebulizer was spun down and the DNA solution recovered. DNA was purified on one QIAQUICK® (Qiagen) PCR purification column and eluted in 30 μl of 10 mM Tris-HCl pH 8.5. 0.5 μg of randomly sheared DNA was used for the labeling and hybridization steps previously described.

After hybridization, the data from the restriction enzyme (RE) digest and randomly sheared samples were compared to determine if there is any difference with sample prep methodology. The comparison of nebulized samples vs. RE digested samples showed a high correlation of fold changes (R squared=0.89). Therefore, there are no major differences with the data when either sample prep method is utilized.

EXAMPLE 4

Genetic Diversity

The methodology outlined in Examples 1-3 were used to generate estimates of copy number variation genetic diversity in select maize genotypes. As shown in the art, research in humans has demonstrated copy number variation between monozygotic twins (Bruder, et al., (2008) *Am J Hum Genetic* 82:763-771).

A. Plant Variation

Figure 3:
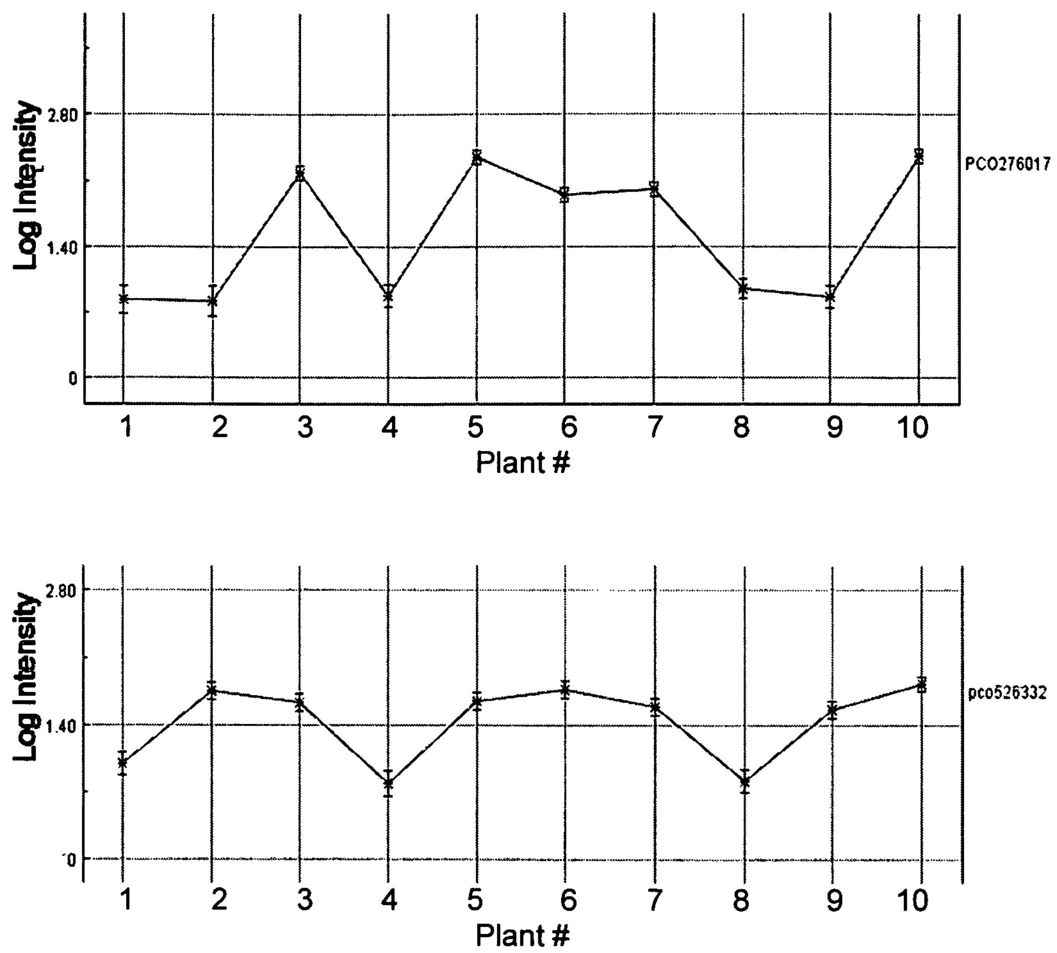
FIG. 3 shows data exemplifying genetic diversity within a maize genotype. Representative data for two oligos showing copy number variation between plants are shown.

DNA from ten maize plants of the same genotype was subjected to comparative genome hybridization and analysis essentially as described in Examples 1-3 to identify putative CNVs between the individual plants. The observed variation between plants ranges from 0.09% to 0.38%. Technical variation was also determined, and estimated to be 0.08%. Representative data for two putative CNVs showing Log Intensity vs. plant number is shown in FIG. 3.

B. Variation within a Heterotic Group

Figure 4:
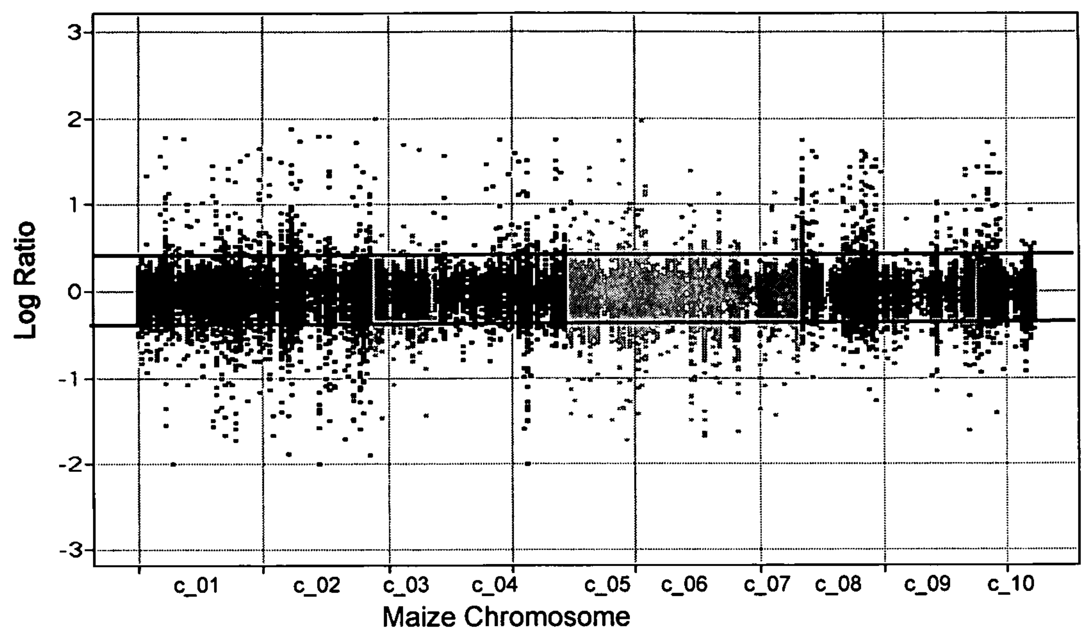
FIG. 4 shows data exemplifying genetic diversity within a maize heterotic group. Representative data showing copy number variation between two stiff stalk maize inbreds are shown.

In order to estimate the diversity within a maize heterotic group, DNA isolated from two inbreds from the stiff stalk heterotic group was analyzed as described in Examples 1-3 to identify copy number variations. The observed variation was plotted as a log ratio of the two genotypes for each individual chromosome as shown in FIG. 4.

C. Variation Between Heterotic Groups

Figure 5:
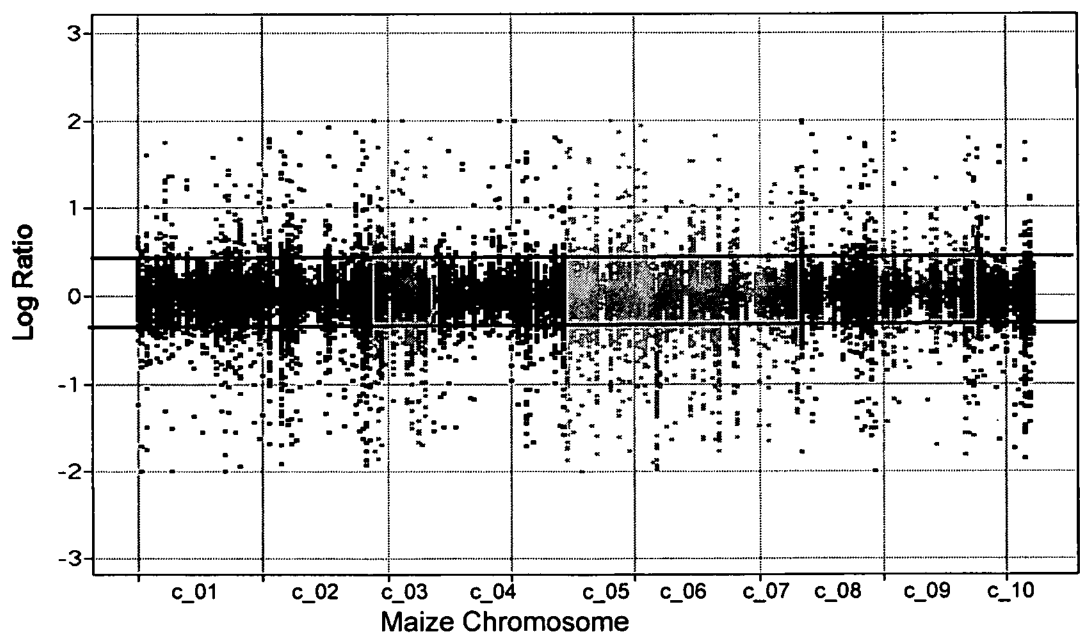
FIG. 5 shows data exemplifying genetic diversity between two maize heterotic groups. Representative data showing copy number variation between a stiff stalk maize inbred and a non-stiff stalk maize inbred are shown.
Figure 6:
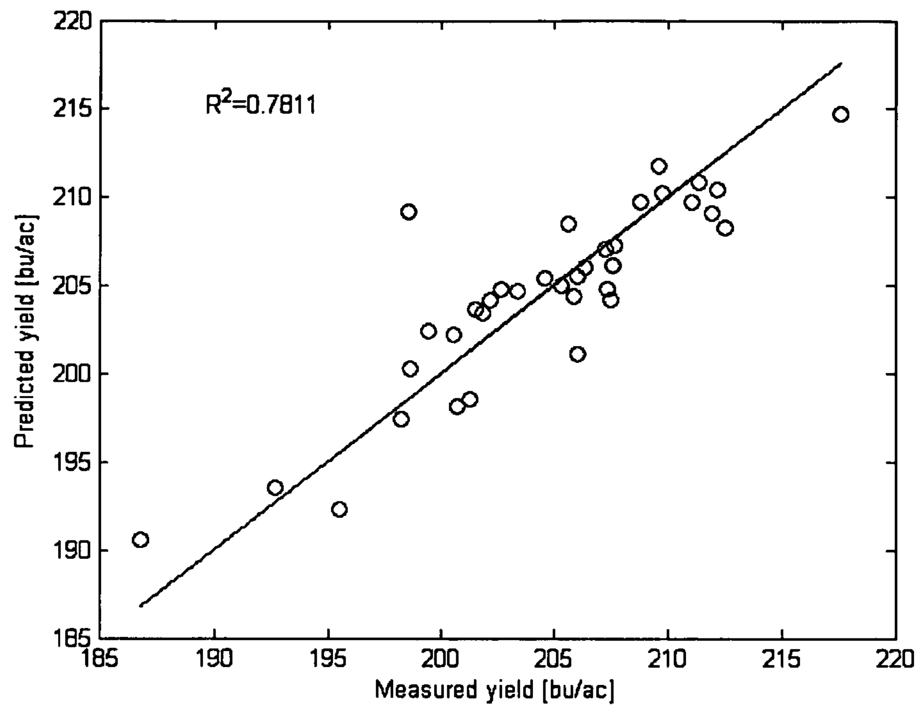
FIG. 6 shows yield prediction data from copy number variations detected by comparative genomic hybridization.
Figure 7:
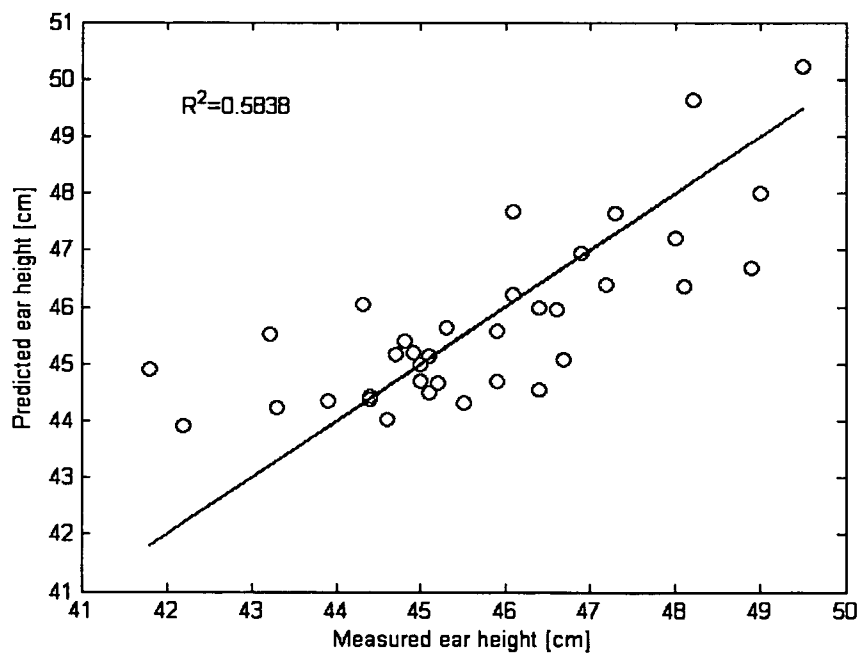
FIG. 7 shows ear height prediction data from copy number variations detected by comparative genomic hybridization.
Figure 8:
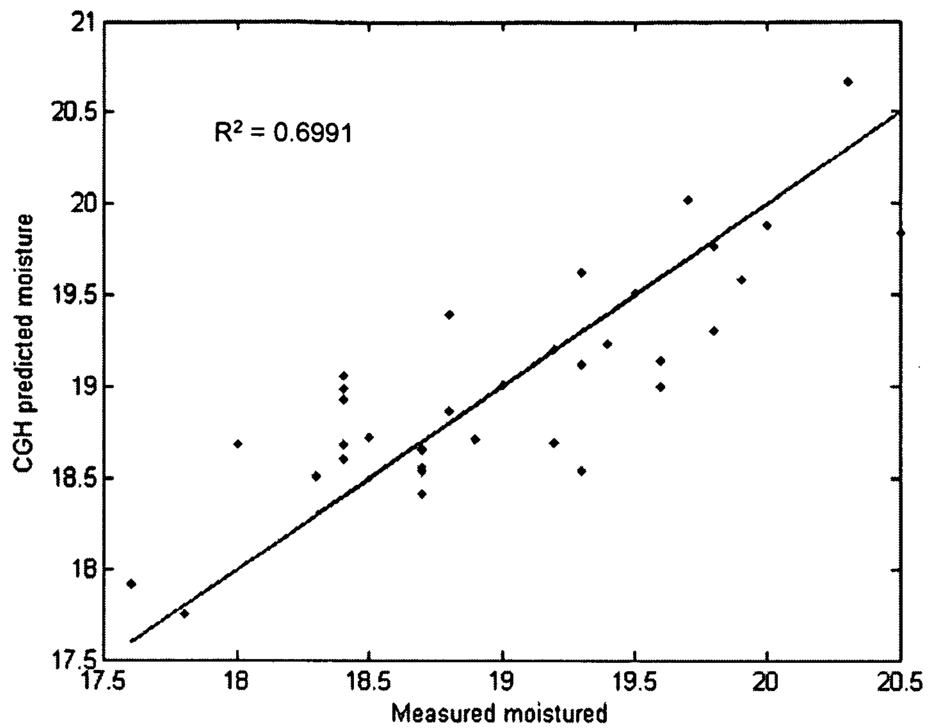
FIG. 8 shows moisture prediction data from copy number variations detected by comparative genomic hybridization.
Figure 9:
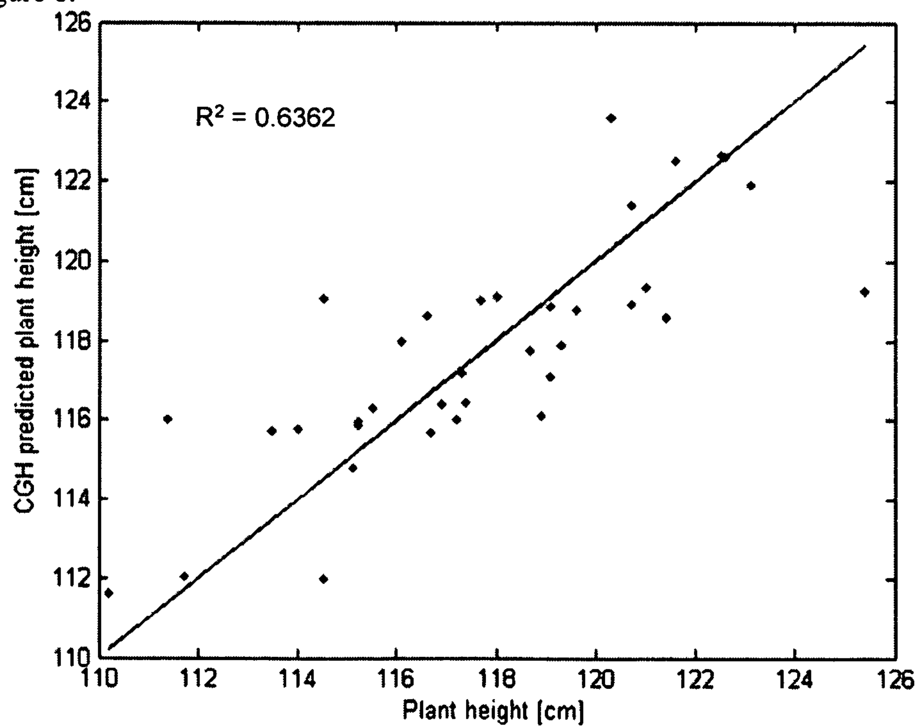
FIG. 9 shows plant height prediction data from copy number variations detected by comparative genomic hybridization.

In order to estimate the diversity between two maize heterotic groups, DNA isolated from two inbreds, a stiff stalk inbred, and a non-stiff stalk inbred. The DNA was analyzed as described in Examples 1-3 to identify copy number variations. The observed variation was plotted as a log ratio of the two genotypes for each individual chromosome as shown in FIG. 5.

EXAMPLE 5

Chemometrics

Chemometrics have been applied to the hybridization data to identify the oligos likely to be predictive of at least one heterotic phenotype. The analyses described in Example 2 are also chemometric methods that can be applied to genomic structural variation data.

In general, the objective of the chemometric analyses was to predict plant performance based on CGH intensity data. The analyses were optimized through selection of variables, including preprocessing and prediction based algorithms. Analysis was validated using one or more tests including a 'leave one out' calibration test, prediction for a new sample in the heterotic group, and/or comparison of selected oligonucleotides to known markers or mapping data. Preprocessing includes steps such as classification of data based on hybridization intensity: no variation in reference CGH intensity; less than a 10-fold change in intensity; and more than a 2-fold change in intensity. Prediction based variable selection includes use of a genetic algorithm (GA), which is a slower but more thorough method, or use of variable importance projection (VIP), which is a rapid early assessment using predictive ranking.

CGH data was generated essentially as described in Example 1, by hybridization against maize CGH arrays in 2×105K format. Samples were for CGH were taken from 14 R2 experiments containing plants from 3 relative maturity groups, representing 181 genotypes (91 stiff stalk, 90 non-stiff stalk inbreds) which produced 914 hybrids. The data was analyzed to identify oligonucleotides associated with heterosis using phenotypic data including yield, ear height, moisture, test weight, stay green, plant height, stock lodging, and root lodging. Data from this analysis was cross-validated with mapping data when available. For stiff-stalk inbred A vs. 36 non-stiff stalk inbreds, putative predictive oligo sets for yield, ear height, moisture, and plant height were identified.

In this experiment, changes in the approach were taken to include an additional more rapid method of variable selection. CGH intensities were included in the multivariate regression if there was no variation in the reference hybridization data set, the relative intensity for each of the oligos for each inbred was less than ten for all the oligos but greater than two for at least one quarter of the inbreds. For the test set "Inbred A", 34541 out of the 103250 available oligos that met these preprocessing selection criteria. A PLS regression model was built for each of the phenotypic traits yield, ear height, plant height and moisture using one latent variable. The variable importance in the projection (VIP score) was then calculated and used to select oligos for an additional model. The VIP threshold for inclusion in the model was set at least higher than 1 and as high as 10. A second model was then built with the reduced number of variables and a second VIP selection was performed with these variables using similar criteria as the first. After the second variable selection iteration the leave-one-out cross-validation was performed to estimate the prediction error for each inbred. The predicted traits are compared to the measured traits in the FIGS. 6-9. The chemometric analysis data for Inbred A vs. 36 non-stiff stalk inbreds are summarized in Table 1 below. Within these predictive oligo sets, there 2 oligos found in common in the yield and plant height prediction sets, indicating that some traits may be correlated. A regression of plant height vs. yield data gave an $R^2$ value of 0.310.

TABLE 1

| Trait Prediction | # Oligos | $R^2$ | Validation |
|---|---|---|---|
| Yield | 18 | 0.7811 | 4 oligos mapped to region associated with yield |
| Ear Height | 8 | 0.5838 | 5 oligos mapped to region associated with ear height |
| Moisture | 18 | 0.6991 | 8 oligos mapped to region associated with moisture |
| Plant Height | 32 | 0.6362 | 11 oligos mapped to region associated with plant height |

EXAMPLE 6

Whole Genome Sequencing

Other methods that may be used for the detection of genomic structural variants, such as copy number variations, insertions, deletions and nucleotide polymorphisms (SNPs) include methods for direct comparative DNA sequencing of genomes. Direct comparative sequencing can be accomplished in a number of ways known to those skilled in the art, including but not limited to the approaches below.

For example, whole genome shotgun sequencing and assembly using fluorescent dideoxynucleotide sequencing can be used to detect and characterize structural differences. The genomes of the individual plant lines differing in their genotypes, as determined by genetic marker analysis or pedigree analysis, are sequenced and then compared to each other using available bioinformatic software tools. Any differences are catalogued by type and genomic locations, and their numbers in each category are reported for analysis, for example as described in Examples 2 and/or 5

Whole genome shotgun sequencing using ultra-high throughput technologies, such as the system provided by Illumina, Inc. (www.illumina.com), can be used to produce a plurality of sequences from the genomes of individual plant lines. Sequencing reads produced by this approach are assembled, and analyzed as indicated above. Optionally or in addition, the catalog of the sequence fragments obtained, or of sub-sequences within them (k-mers) is prepared and the two catalogs from two different individuals can be compared. The differences in the number of fragments in each category are noted, and statistical analysis is performed to estimate confidence intervals for these abundance differences. The catalog of the differences meeting statistical confidence criteria is submitted to the analysis as described in Examples 2 and 5, or equivalent methods in the art.

Alternatively, subsets of each genome may be sequenced. For example, a subset can be individual chromosomes obtained by chromosome sorting, genome segments selected by hybridization and subsequent elution from microarrays, or a subset generated by any other method known to those skilled in the art. The catalog of the differences for the subsets of each genome meeting statistical confidence criteria is submitted to the analysis as described in Examples 2 and/or 5, or other equivalent methods. In some examples alternative methods of complete or partial genome sequencing may also be used, providing the methods can produce a catalog of differences in sequences of the genomes being compared.

In one example the direct whole genome sequence involves the following steps:

1) isolate genomic DNA;

2) prepare genomic DNA for sequencing, optionally tag the sequence(s);

3) sequence genomic DNA from step 1 (sequencing method may tag polynucleotides);

4) map sequences to the genome and count occurrence of tags;

5) after normalization of the data, compare the tags between samples to determine CNV;

6) apply data analysis methods (e.g., Example 2 and/or Example 5) to relate the CNVs observed to at least one heterotic phenotype.

Optionally, the isolated genomic DNA from step 1 or step 2 could be processed to remove repetitive sequences or otherwise reduce the complexity of the sample before sequencing. For example oligos to the repetitive regions could be synthesized and tagged with a biotin molecule. The biotinylated oligos are added to the DNA, and the sample applied to a streptavidin column. The flow-through sample of non-repetitive DNA is collected for further analysis. In another example, a microarray that targets the repetitive regions is created. The DNA sample is hybridized to the array such that the unbound fragments are collected and used for sequencing. In another method, the genomic DNA could be digested using a restriction enzyme, and then sequencing initiated from the RE site.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the appended claims. As used herein and in the appended claims, the singular forms “a”, “an”, and “the” include plural reference unless the context clearly dictates otherwise. Thus, for example, reference to “a plant” includes a plurality of such plants; reference to “a cell” includes one or more cells and equivalents thereof known to those skilled in the art, and so forth.

What is claimed is:

1. A method for predicting the heterotic phenotype of progeny plants with unknown heterotic phenotypes, the method comprising:

a) obtaining sample genomic DNA from a plurality of inbred parental plants from a plurality of crosses, wherein each of said crosses produces hybrid progeny plants possessing a known heterotic phenotype;

b) performing a comparative genomic hybridization technique on the sample genomic DNA to detect DNA copy number variations between genomes of said plurality of inbred parental plants, wherein said comparative genomic hybridization technique comprises hybridization of said sample genomic DNA to a plurality of oligonucleotide probe molecules, wherein each of said oligonucleotide probe molecules is between about 20 and about 100 nucleotides in length, wherein the hybridization of sample genomic DNA to each of said oligonucleotide probe molecule produces a hybridization intensity, and wherein said DNA copy number variation is determined by comparing the hybridization intensities (i) between at least two genomic DNA samples from said inbred parental plants or (ii) between at least one genomic DNA sample from said inbred parental plants and a reference sequence;

c) identifying a subset of the copy number variations that predicts the known heterotic phenotype in the hybrid progeny plants, wherein said subset is identified by relating the detected copy number variations to the known heterotic phenotypes using an iterated evolutionary computational approach; and d) utilizing the subset of copy number variations to predict a heterotic phenotype of hybrid progeny plants derived from an additional cross of inbred parental plants, wherein the heterotic phenotype of hybrid progeny plants derived from said additional cross is unknown, and wherein the presence or absence of each of said identified copy number variations is known for each inbred parental plant from said additional cross; and e) crossing the inbred parents of said additional cross to produce a hybrid progeny plant with the heterotic phenotype.

2. The method of claim 1, wherein the probe molecules hybridize to coding regions or other non-repetitive genomic DNA sequences.

3. The method of claim 1, wherein the hybrid progeny plant is maize.

* * * * *